United States Patent [19]

Maurer et al.

[11] Patent Number: 4,822,936

[45] Date of Patent: Apr. 18, 1989

[54] SELECTIVE HYDROGENATION OF PHENYLACETYLENE IN THE PRESENCE OF STYRENE

[75] Inventors: Brian R. Maurer; Mercedes Galobardes, both of Midland, Mich.

[73] Assignee: The Dow Chemical Company, Midland, Mich.

[21] Appl. No.: 89,292

[22] Filed: Aug. 25, 1987

[51] Int. Cl.$^4$ .............................................. C07C 5/03
[52] U.S. Cl. ................................................... 585/259
[58] Field of Search ................................. 585/259, 260

[56] References Cited

U.S. PATENT DOCUMENTS

| | | | |
|---|---|---|---|
| 3,076,858 | 2/1963 | Frevel et al. | 585/262 |
| 3,327,013 | 6/1967 | Frevel et al. | 585/271 |
| 3,634,536 | 1/1972 | Frevel et al. | 585/261 |
| 3,682,585 | 8/1972 | Frevel et al. | 423/219 |
| 3,897,511 | 7/1975 | Frevel et al. | 423/245 |
| 3,912,789 | 10/1975 | Frevel et al. | 585/259 |
| 4,101,451 | 7/1978 | Frevel et al. | 502/315 |
| 4,129,605 | 12/1978 | Tabler et al. | 585/259 |
| 4,389,517 | 6/1983 | Priddy et al. | 526/64 |
| 4,440,956 | 4/1984 | Couvillion | 585/260 |
| 4,493,906 | 1/1985 | Couvillion | 502/346 |

FOREIGN PATENT DOCUMENTS 61-191627 8/1986 Japan .

*Primary Examiner*—Curtis R. Davis
*Attorney, Agent, or Firm*—Charles J. Enright

[57] ABSTRACT

A process for hydrogenating phenylacetylene in the presence of an excess of styrene by contacting a mixture of hydrogen and the phenylacetylene with a catalyst obtained by the reduction of a copper compound on a support.

10 Claims, No Drawings

SELECTIVE HYDROGENATION OF PHENYLACETYLENE IN THE PRESENCE OF STYRENE

FIELD OF THE INVENTION

This invention relates to the selective hydrogenation of phenylacetylenes such as phenylacetylene and alkylphenylacetylenes (hereafter phenylacetylenes and alkylphenylacetylenes are referred to as "phenylacetylene") in the presence of styrene-containing substances such as styrene, crude styrene monomer or methyl styrene (hereafter styrenes are referred to simply as "styrene").

BACKGROUND OF THE INVENTION

Phenylacetylene is a common impurity in styrene produced by dehydrogenation of ethylbenzene. The phenylacetylene is produced in the monomer synthesis step as excessive dehydrogenation of ethylbenzene takes place. Commercial grade monomers may contain up to about 150 ppm of phenylacetylene.

Low phenylacetylene feedstocks may be useful for anionic polymerizations. See Priddy et al., U.S. Pat. No. 4,389,517, which is incorporated herein by reference.

Phenylacetylene contained in said styrene-containing substances may be removed by selective hydrogenation. However, hydrogenation of vinyl group of styrene competes with the desired hydrogenation of the acetylenic group. A selective catalyst is desired for the reaction because the concentration of phenylacetylene is low compared to the styrene. Poor selectivity results in an undesired conversion of styrene to ethyl benzene or may result in the formation of polymers and tars.

The previous art of hydrogenating phenylacetylene in styrene feedstreams has primarily focused on the use of palladium-based hydrogenation catalysts. Although phenylacetylene levels can be reduced to nondetectable levels (<2 ppm) with palladium-based catalysts, a large stoichiometric excess of hydrogen is necessary. This large excess of hydrogen leads to additional hydrogenation of styrene monomer to ethylbenzene thereby decreasing the selectivity of the catalyst.

For example, Japanese Kokai No. 84-216838 discloses a method for selectively hydrogenating phenylacetylene using catalysts, which contained at least one metal selected from a group comprising Pd, Pt, Ir, Rh and Ru and at least one element selected from a group comprising Pb, Bi, P, Sb, As, Te and S. Said method is not sufficiently selective for hydrogenating phenylacetylene.

U.S. Pat. Nos. 4,493,906 and 4,440,956 disclose methods and supported copper catalysts for selectively hydrogenating acetylenes in the presence of olefins and in particular diolefins. However, the processing conditions and hydrogenation requirements are different than for the phenylacetylene hydrogenation system. In the case of butadiene streams, hydrogenation temperatures of 50° C. with approximately 250 psi hydrogen are required to maintain the necessary solubility of hydrogen in the feedstream. These somewhat harsh conditions lead to the formation of "green oils" which primarily result from polymerization products. These "green oils" decrease the lifetime of the catalyst.

SUMMARY OF THE INVENTION

An improvement over the art is achieved by a process for hydrogenating phenylacetylenes in the presence of an excess of styrene by contacting a mixture of hydrogen and the phenylacetylene with a catalyst obtained by the reduction of a copper compound on a support.

Preferably, one may employ a γ-alumina (γ is gamma) as described in U.S. Pat. No. 4,493,906 which may contain up to 50 percent, preferably 35 percent by weight or less of γ-alumina, and preferably, a special grade of γ-alumina (γ-$Al_2O_3$), one which has low, less than 0.15 weight percent each of silicon as $SiO_2$ and sodium as $Na_2O$, and preferably, a sodium content less than about 0.10 percent, less than 0.01 weight percent sulfur and less than 0.06 weight percent iron as $Fe_2O_3$, and additionally has a surface area of between about 68 and 350 m2/g and wherein between about 98 percent and about 40 percent of the pores have a pore diameter between about 40 Å and 120 Å and not more than 25 percent nor less than 2 percent have a pore diameter between 1000 Å to 10,000 Å. This catalyst support, when coated with about 3 to 13 weight percent copper metal may permit reaching lower phenylacetylene levels with less styrene loss than prior art processes and the catalyst may be regenerable to high activity over several cycles.

More preferably, one may employ a catalyst as described in U.S. Pat. No. 4,440,956 comprising a mixture of finely divided copper metal and minor amounts of at least one polyvalent activator metal selected from the group consisting of silver, platinum, palladium, manganese, cobalt, nickel, chromium and molybdenum, dispersed on an aluminum oxide support, said support being a γ-alumina as defined by the Joint Committee on Powder Diffraction Standards, #29-63, of high purity having a surface area of between about 68 and about 350 m2/g, and 90 to 60 percent of the pores have a pore diameter between 1000 Å to 100,000 Å, a silicon content as $SiO_2$ of less than about 0.15 weight percent, a sodium content as $Na_2O$ of less than about 0.15 weight percent, a sulfur content less than about 0.01 weight percent and an iron content as $Fe_2O_3$ of less than about 0.06 weight percent, said γ-alumina may contain up to 35 percent by weight of α-alumina.

Because the high selectivity for hydrogenation of phenylacetylene, this catalyst may lead to a low loss of styrene and little side reactions such as hydrogenation of styrene.

Catalyst life may be extended because the present invention may not cause the cleavage of carbon bonds, the formation of gummy substances, and the formation of carbonaceous substances.

The present catalyst system is cheaper than hydrogenation catalysts using noble metals.

Because the catalyst may be active and selective, it may be used at lower temperatures which may lead to less polymer formation during the reaction.

DETAILED DESCRIPTION

The Catalyst Support

Usable supports include various types of metal oxides, silica and activated charcoal, among which alumina, and particularly, the aforementioned γ-alumina is preferred.

It has been found that during use, the γ-alumina described above undergoes a phase change, probably due to thermal treatment during operation and regeneration. Thus, a γ-alumina, within the scope above defined, will undergo a gradual change during an extended period of time, multiple-cycle (with regeneration) run, to analyze about 35 percent α-alumina with an attendant reduction in surface area from about 165 m2/g to about 68 m2/g. There is also a change in the pore volume distribution associated with the reduction in surface area and presence of α-alumina. However, the pore sizes remain within the aforedefined range. Thus, while it is preferred to start with a relative high purity γ-alumina having the above described properties and physical characteristics, it is to be understood that a carrier or support may be a combined unitary alumina consisting of a high purity alumina as above defined but having up to 50 percent γ-alumina in admixture with γ-alumina. Such a support can be readily obtained by thermal treatment of γ-alumina of the requisite purity in the presence of cuprous oxide. The phase change apparently occurs during the oxidation and/or reduction during regeneration. Presumably, the cuprous oxide acts as a seed or catalyst to effectuate the phase change from γ to α state. However, no specific theory based on scientific data of how such a change occurs can yet be set forth. While the aforestated procedure appears to effect the change, other methods may be available from those skilled in the art of alumina production.

The catalyst carrier or support which appears to be at least preferred to obtaining the aforesaid results is a special grade of γ-alumina (γ-Al$_2$O$_3$) prepared by decomposing trialkyl alumina to γ-aluminum monohydrate, then calcining the γ-aluminum monohydrate to γ-alumina. This process produces a grade of γ-alumina normally not obtainable from naturally occurring aluminum-containing ores and which has, when pressed or extruded into pellets, a higher purity than naturally occurring alumina, and a pore size and pore size distribution sufficiently different from that obtainable using naturally occurring aluminas and converting them to γ-alumina. The most ready source of catalyst support size pellets is from The Harshaw Chemicals Co. sold as 3438T, Norton Company as SA6173 and Calsicat Division, Mallinckrodt Chemical Works as CALSICAT Type A and AA. Although, Conoco Chemicals Division, Conoco, Inc., manufactures a powder, CATAPAL type SB, which has been found suitable and is believed to be the precursor powder for the three pellet producers, pellets produced by Conoco are not readily available except through the three pelletizers.

In order to identify each support, the following table of physical properties is set forth.

|  | wt % Na$_2$O | wt % SiO$_2$ | wt % Fe$_2$O$_3$ | Surface Area M$^2$/g | Pore Volume cc/g | Bulk Density g/cc | Sulfur |
|---|---|---|---|---|---|---|---|
| CALSICAT Type A | .005 | .01 | (<.01) | 200 | .50 | .80 | (.01) |
| HARSHAW Al-3438T | (.005) | (.01) | <.01 | 175 | .50 | .78 | (.01) |
| CATAPAL Type SB | .004 | .008 | .005 | 241 | .57 | .79 | .01 |
| CALSICAT Type AA | .07 | .12 |  | 215 | .70 | .63 | — |
| NORTON SA-6173 | .015 | .09 | .06 | 240 | .56 | .69 | — |
| REYNOLDS RA-1 [1] | .35 | 66 ppm | 190 ppm | 213 | .18 | .88 | — |

[1] Conventional γ-AlOOH support (non-preferred)

CATALYSTS

Catalysts usable in the present invention are prepared by supporting copper or at least one type of inorganic salt, organic acid salts or oxides of copper on a support and reducing to zero-valent copper using an appropriate reducing agent.

The compositional ratio of copper to support can be selected from the range of 1 to 48 weight percent, preferably 5 to 30 weight percent. Methods for preparing catalysts are not particularly limited, but can be any proper methods for supporting catalysts. For example, catalysts can be prepared by the following method. A fixed amount of solution of such acid- or water-soluble salts as copper chloride, copper nitrate, copper acetate and copper sulfate is impregnated in alumina support, and said copper salts are heated in air or an inert gas containing oxygen at a high temperature. Subsequently, said copper oxides are reduced to mono-valent or metallic copper by a dry or wet method using such appropriate reducing agents a hydrogen, hydrazine, formaldehyde and sodium formate.

KLP is a copper-based catalyst (8 percent Cu/Al$_2$O$_3$), available from The Dow Chemical Company. The catalyst contains activator metals which help maintain acceptable catalyst lifetimes. The composition of the KLP catalyst is described in U.S. Pat. Nos. 4,493,906 and 4,440,956. Dow's Type Q5 catalyst is an example of a copper-based catalyst which has fewer activator metals. The comparative compositions are set out in the table.

| Metal | KLP (wt %) | Q5 (wt %) |
|---|---|---|
| Cu | 8.39 | 8.81 |
| Ni | 0.22 | 0.41 |
| Co | 0.09 | 0.16 |
| Mn | 0.07 | 0.08 |
| Ag | 0.04 | — |
| Cr | 0.06 | — |
| Total | 8.87 | 9.46 |

While Q5 is an active catalyst it must be regenerated more often than the KLP. When Q5 copper catalyst is used to hydrogenate phenylacetylene from styrene, the catalyst slowly deactivates over time. Although the catalyst becomes deactivated, it is not found to be poisoned. The Q5 catalyst may be easily regenerated and reactivated to nearly reobtain its initial activity. Small scale and pilot plant runs of KLP catalyst indicate that there may be a slower decrease in catalyst performance.

EXAMPLE 1

In accordance with the present invention, 400 g of γ-Al$_2$O$_3$ of Norton SA6173 obtained from Norton Chemical Company, as 1/16" diameter extrudates about ¼" long has the following properties:

| X-ray Diffraction pattern matches Joint Committee on Powder Diffraction standards #29-63 | |
| --- | --- |
| wt % Na$_2$O | 0.015 |
| wt % SiO$_2$ | — |
| wt % Fe$_2$O$_3$ | 0.006 |
| Surface Area (m$^2$/g) | 240 |
| Pore volume (cc/g) | 0.56 |
| Bulk density (g/cc) | 0.69 |

75% of its pores were less than 75Å
82% of its pores were less than 100Å
18% of the pores were between 102Å and 8390Å

The unburdened support is impregnated with a solution consisting of:

| | Grams |
| --- | --- |
| Cu(NO$_3$)$_2$.2½H$_2$O | 140 |
| H$_2$O | ca. 40 |

The resulting solution is poured over 400 g of the support in a beaker while stirring to obtain even distribution. When all of the solution has been absorbed, the support is dried overnight at 110° C., then calcined at 400° C. for about 6 hours.

EXAMPLE 2

In accordance with the present invention, 300 g of γ-Al$_2$O$_3$ obtained from Conoco Chemicals Division, Conoco, Inc., as 0.125 inch diameter by 0.25 inch long pellets identified as CATAPAL SB has the following properties:

| X-ray Diffraction Pattern Matches Joint Committee on Powder Diffraction Standards #29-63 | |
| --- | --- |
| wt % Na$_2$O | 0.004 |
| wt % Sulfur | 0.01 |
| wt % SiO$_2$ | 0.006 |
| wt % Fe$_2$O$_3$ | 0.005 |
| Surface Area (m$^2$/g) | 241 |
| Pore volume (cc/g) | 0.57 |
| Bulk density (g/cc) | 0.79 |

75% of its pores are less than 75Å
82% of its pores are less than 100Å
18% of the pores are between 102Å and 8390Å

The unburdened support is impregnated with a solution consisting of:

| | Grams | Parts by Weight |
| --- | --- | --- |
| Cu(NO$_3$).2½H$_2$O | 113 | 0.9135 |
| Ni(NO$_3$)$_2$.6H$_2$O | 4 | 0.0323 |
| H$_2$O | ca. 40 | |
| HNO$_3$ | 59 | |
| Mn(NO$_3$)$_2$ 50% solution | 3.1 | 0.0250 |
| AgNO$_3$ | 0.2 | 0.0016 |
| Cr(NO$_3$)$_3$.9H$_2$O | 1.7 | 0.0137 |
| Co(NO$_3$)$_2$.6H$_2$O | 1.7 | 0.0137 | in sufficient water of a pH of 6.5–7.5 to wet the surface of said support. Solubilization of the numerous metal salts is obtained by gentle heating. The resulting solution is poured over 300 g of the support in a beaker while stirring to obtain even distribution. When all of the solution has been absorbed, the support is dried overnight at 110° C., then calcined at 400° C. for about 6 hours.

EXAMPLE 3

To 400 g of a catalyst support obtained from Calsicat Division, Mallinckrodt Chemical Works, identified as CALSICAT Type A having the following physical properties as 0.125 inch pellets:

| X-ray Diffraction Pattern Matches Joint Committee on Powder Diffraction Standards #29-63 | |
| --- | --- |
| wt % Na$_2$O | 0.005 |
| wt % Sulfur | 0.01 |
| wt % SiO$_2$ | 0.01 |
| wt % Fe$_2$O$_3$ | (<0.1) |
| Surface Area (m$^2$/g) | 200 |
| Pore volume (cc/g) | 0.50 |
| Bulk density (g/cc) | 0.8 |

75% of its pores were less than 75Å
82% of its pores were less than 100Å
18% of the pores were between 102Å and 8390Å is added the following liquid mixture:

| | Grams | Parts by Weight |
| --- | --- | --- |
| Cu(NO$_3$)$_2$.2½H$_2$O | 140 | 0.9164 |
| Ni(NO$_3$)$_2$.6H$_2$O | 4.75 | 0.0311 |
| H$_2$O | ca. 50 | |
| HNO$_3$ (conc.) | 71 | |
| Mn(NO$_3$)$_2$ 50% solution | 4 | 0.0262 |
| AgNO$_3$ | 0.25 | 0.0016 |
| Cr(NO$_3$)$_3$.9H$_2$O | 2 | 0.0131 |
| Co(NO$_3$)$_2$.6H$_2$O | 2 | 0.0131 | in sufficient water of a pH of 6.5–7.5 to wet the surface of said support with stirring and heating, 50° C.–60° C., until the liquid is absorbed. Thereafter, the wetted support is dried in an oven at 110° C. for 2 hours, then placed in a furnace at 400° C. for about twenty hours. The catalyst is removed from the furnace and cooled.

EXAMPLE 4

A catalyst prepared from a high purity Norton SA6173 1/16" extrudate upon which copper and promoter metals are impregnated, is calcined at 400° C. for 8 hours. The proportions employed to prepare this catalyst are:

| | Grams |
| --- | --- |
| Norton SA6173 1/16" | 4800 |
| Cu(NO$_3$)$_2$.2½H$_2$O | 1680 |
| Ni(NO$_3$)$_2$.6H$_2$O | 57 |
| H$_2$O | ca 600 |
| HNO$_3$ (conc.) | 85 |
| Mn(NO$_3$)$_2$ 50% solution | 48 |
| AgNO$_3$ | 3 |
| Cr(NO$_3$)$_3$.9H$_2$O | 24 |
| Co(NO$_3$)$_2$.6H$_2$O | 24 |

In evaluating the performance of the catalyst and its support in respect to materials of construction, it is found that the materials of construction for the reactor may be important if long, 14-day, on-stream cycles are desired. Thus, when one employs a stainless steel containing nickel, the efficiencies of the catalysts of the present invention are somewhat reduced due to the necessity to regenerate the catalyst more often. This phenomenon may be overcome when carbon steel is employed as the material of construction for the reactor.

Another point which long run data establishes is that steam regeneration may reduce the life of a catalyst by a loss of surface copper and an increase in copper crystallite size following regeneration and/or oxidation of the catalyst.

THE HYDROGENATION

The hydrogenation temperature is below about 200° C., preferably in the range of from about 5° C. to about 100° C. and most preferably from about 5° C. to about 35° C. Too high a reaction temperature is not desirable because hydrogenation and polymerization of styrene may take place. The hydrogenation pressure is in the range of ambient to slight pressure, preferably 0 to 10 psig and most preferably at 0 psig.

The liquid space velocity (LHSV) is in the range of 1 to 500 hr$^{-1}$, preferably 1 to 200 hr$^{-1}$. When the liquid space velocity is too high, the conversion of phenylacetylene decreases. When it is too low, hydrogenation of styrene takes place and the yield of styrene decreases.

The amount of hydrogen to be fed is normally in the range of one to 100 times the molar concentration of phenylacetylene. Generally the amount of hydrogen that dissolves in the reactants is sufficient to carry out the reaction. A large excess of hydrogen may hydrogenate the styrene.

Since a 2- to 3-fold excess of hydrogen is soluble in styrene monomer at ambient conditions, more mild hydrogenation conditions may be employed. These less harsh conditions can significantly diminish the amount of polymer formation in the styrene hydrogenation process. A 10-30 ppm polymer formation may be obtained and preferably a 0-2 ppm polymer formation may be obtained.

PROCESS EXAMPLE 5

The catalyst of Example 4 (2000 g), is charged into a 2" diameter by 48" length stainless steel bed. The catalyst is then heated to 270° C. under nitrogen (0.5 SCFH) for approximately 2 hours, held at 270° C. while in contact with a 5 percent H$_2$/N$_2$ gas mixture (0.5 SCFH) for approximately 8 hours, and cooled to room temperature under nitrogen. The temperature should be carefully monitored to prevent sintering of the catalyst. Complete metal reduction of the catalyst is desirable. Without complete metal reduction, the catalyst lifetime may be shortened. A styrene stream with 110 weight ppm of phenylacetylene is used with a hydrogen flow rate of 50 cc/min. The styrene is exposed to an ambient temperature, adiabatic flash to remove dissolved oxygen, and the feedstream flow rate is set at 35 lb/hr. A typical styrene stream used contains about 110 ppm phenylacetylene. To minimize the amount of polymer formation due to the heat of adsorption, the bed is thoroughly flushed with ethylbenzene prior to use. Capillary gas chromatography data show that when using KLP catalyst the phenylacetylene is reduced to nondetectable (<2 ppm) levels, and the polymer level is measured as 0-2 ppm. The experiment is conducted for approximately 72 hours, and no decrease in catalyst activity is observed.

What is claimed is:

1. A process comprising hydrogenating phenylacetylene in the presence of an excess of styrene by contacting a mixture of hydrogen and the phenylacetylene at a hydrogenation temperature of less than about 35° C. with a catalyst obtained by the reduction of a copper compound on a support.

2. The process of claim 1 wherein the support is a γ-alumina which contains 50 percent by weight or less of γ-alumina and less than 0.15 weight percent each of silicon as SiO$_2$ and sodium as Na$_2$O, and less than 0.01 weight percent sulfur and less than 0.06 weight percent iron as Fe$_2$O$_3$, and has a surface area of between about 68 and 350 m2/g and wherein between about 98 percent and about 40 percent of the pores have a pore diameter between about 40 Å and 120 Å and not more than 25 percent nor less than 2 percent have a pore diameter between 1000 Å to 10,000 Å.

3. The process of claim 2 wherein the catalyst comprises a mixture of finely divided copper metal and minor amounts of at least one polyvalent activator metal selected from the group consisting of silver, manganese, cobalt, nickel and chromium.

4. The process of claim 1 wherein the hydrogenation is carried out at a pressure of less than about 10 psig.

5. The process of claim 4 wherein the hydrogenation is carried out at a pressure of about zero psig.

6. The process of claim 4 wherein the hydrogen is present in an amount that dissolves in the reactants and is sufficient to hydrogenate the phenylacetylene.

7. The process of claim 6 wherein less than 30 ppm polymer is formed.

8. The process of claim 7 wherein less than 10 ppm polymer is formed.

9. The process of claim 8 wherein less than 2 ppm polymer is formed.

10. The process of claim 7 wherein the phenylacetylene is reduced to less than 2 ppm.

* * * * *